United States Patent
Mlynski et al.

(10) Patent No.: US 7,065,404 B2
(45) Date of Patent: Jun. 20, 2006

(54) RATE-ADAPTIVE CARDIAC PACEMAKER

(75) Inventors: Michael Frank Mlynski, Aachen (DE); Bjorn Henrik Diem, Aachen (DE); Walter Ameling, Aachen (DE); Peter Hanrath, Aachen (DE)

(73) Assignee: Biotronik Mess-und Therapiegereate GmbH & Co. (DE)

( * ) Notice: Subject to any disclaimer, the term of this patent is extended or adjusted under 35 U.S.C. 154(b) by 596 days.

(21) Appl. No.: 10/234,023

(22) Filed: Sep. 3, 2002

(65) Prior Publication Data

US 2003/0105498 A1    Jun. 5, 2003

(30) Foreign Application Priority Data

Sep. 6, 2001    (DE) ............................... 101 44 442

(51) Int. Cl.
*A61N 1/362* (2006.01)
(52) U.S. Cl. ........................................................ 607/9
(58) Field of Classification Search ................ 607/9, 607/14, 17, 25
See application file for complete search history.

(56) References Cited

U.S. PATENT DOCUMENTS 4,503,857 A * 3/1985 Boute et al. .................... 607/9
4,856,524 A   8/1989 Baker, Jr.

(Continued)

FOREIGN PATENT DOCUMENTS

DE    100 29 677 A1    12/2000

(Continued)

OTHER PUBLICATIONS

Duru, et al., "Clinical Evaluation of a Pacemaker Algorithm that Adjusts the Pacing Rate During Sleep Using Activity Variance," PACE, p. 1509-15, (Oct. 21, 2000).

*Primary Examiner*—Robert E. Pezzuto
*Assistant Examiner*—Kristen Mullen
(74) *Attorney, Agent, or Firm*—HahnLoeser & Parks LLP

(57) ABSTRACT

A rate-adaptive cardiac pacemaker has a detection unit 1, an event-determining unit 2, a stimulation control unit 3 and a stimulation unit 11, wherein the event-determining unit 2 is connected to the detection unit 1 and the stimulation control unit 3, and the stimulation unit 11 is connected to the stimulation control unit 3. The detection unit 1 detects ECG signals of a heart 100, and the event-determining unit 2, on the basis of the ECG signals detected by the detection unit 1 and signals emitted by the stimulation control unit 3, determines whether a detected event represents a spontaneous or a stimulated event ($A_p$, $A_s$; AES, $V_p$, $V_s$, VES). The stimulation control unit 3 ascertains a stimulation rate based upon a base rate and a physiological demand and varies the base rate based upon the event-determining unit 2 in a first mode, when atrial events occur in such a way that in the case of a spontaneous atrial event a spontaneous interval is prolonged by a first change value and that in the case of a stimulated atrial event a base interval is prolonged by a second change value, whereby in both cases the base rate is lowered, and in a second mode, when ventricular events occur, the stimulation control unit 3 varies the base rate in such a way that in the case of a spontaneous ventricular event the base rate is raised and in the case of a stimulated ventricular event the base rate is lowered. The stimulation unit stimulates the heart in accordance with the signals received from the stimulation control unit 3.

5 Claims, 9 Drawing Sheets

U.S. PATENT DOCUMENTS

| | | |
|---|---|---|
| 4,941,471 A | 7/1990 | Mehra |
| 5,144,949 A | 9/1992 | Olson |
| 5,237,992 A * | 8/1993 | Poore .......................... 607/18 |
| 5,292,340 A | 3/1994 | Crosby et al. |
| 5,312,451 A * | 5/1994 | Limousin et al. ............. 607/15 |
| 5,374,281 A * | 12/1994 | Kristall et al. ................ 607/17 |
| 5,417,714 A * | 5/1995 | Levine et al. .................. 607/9 |
| 5,507,782 A * | 4/1996 | Kieval et al. .................. 607/9 |
| 5,514,164 A | 5/1996 | Mann et al. |
| 5,645,576 A * | 7/1997 | Limousin et al. ............. 607/19 |
| 5,713,929 A * | 2/1998 | Hess et al. .................... 607/14 |
| 5,792,192 A | 8/1998 | Lu |
| 6,078,836 A * | 6/2000 | Bouhour et al. .............. 607/14 |
| 6,408,209 B1 * | 6/2002 | Bouhour et al. .............. 607/19 |

FOREIGN PATENT DOCUMENTS

| | | |
|---|---|---|
| DE | 199 40 952 A1 | 2/2001 |
| EP | 0 448 193 | 9/1991 |
| EP | 0 449 401 B1 | 4/1997 |
| WO | WO 01/05465 | 1/2001 |

* cited by examiner

RATE-ADAPTIVE CARDIAC PACEMAKER

BACKGROUND OF THE ART

In order to be able to program cardiac pacemakers on an individual patient basis and thus to be able to provide each patient with therapies which are matched to the cardiac disease of the patient, cardiac pacemakers (CPM) nowadays have a multiplicity of parameters, by means of which the mode of operation of the pacemaker and therewith the therapy afforded by the pacemaker in operation can be adjusted.

Those parameters are programmed for the first time on an individual patient basis in the implantation procedure. Thereafter at regular intervals (typically every 6 months) the patient comes for so-called post-care investigation in which not only the battery and the set pacing and sensing thresholds are checked but in some circumstances also parameters in regard to altered symptoms are re-adjusted.

That procedure admittedly makes it possible to program patient-specific therapies, but they are fixedly set for the following period of time, up to the next post-care investigation. For that reason, the manufacturers of cardiac pacemakers have already long been endeavoring to continuously automatically adapt the parameters to the current requirements of a patient.

Many rate-adaptive cardiac pacemakers are known, in which a large number of physiological parameters are detected as indicators of the metabolic demand and used to control rate adaptation.

DE 199 40 952 discloses a rate-adaptive cardiac pacemaker in which rate adaptation is effected in dependence on the respiration rate. In that respect the basic starting point involved is the central-nervous coupling of respiration and circulatory activity, in which in particular heart rate, heart beat volume and vasomotor system are of significance as circulation-relevant parameters. Measurement of the respiration rate can be effected by measurements in respect of the intrathoracal and/or intracardial impedance.

EP 0 449 401 also discloses a rate-adaptive cardiac pacemaker which has an impedance system for measuring a right-ventricular (or atrial) volume or a pressure transducer for measuring the right-ventricular (or atrial) pressure and a signal processing unit for beat-wise ("beat-to-beat") extraction of one of the volume or pressure parameters in order thereby to obtain a signal which varies with the respiration rate, and has a peak-to-peak amplitude proportional to the depth of respiration. In that arrangement the signal processing unit is provided to extract the period of the respiration signal and to use the peak-to-peak amplitude and the resulting signals to determine the required stimulation rate for the cardiac pacemaker.

Algorithms for stabilization of the cardiac frequency are known for example from PACE, Vol. 23, October 2000, Part I, pages 1509 ff.

SUMMARY OF THE INVENTION

It is desirable to be able to still further adapt the pacing and sensing properties of cardiac pacemakers to the actual metabolic requirement of a patient and/or to stabilize the cardiac frequency.

Therefore the object of the invention is to improve the rate adaptation properties of rate-adaptive cardiac pacemakers.

The object of the invention is attained by a rate-adaptive cardiac pacemaker having the features of claim 1.

In accordance with the invention, for that purpose, there is provided a rate-adaptive cardiac pacemaker which has a detection unit, an event-determining unit, a stimulation control unit and a stimulation unit, wherein the event-determining unit is connected to the detection unit and the stimulation control unit and the stimulation unit is connected to the stimulation control unit. The detection unit detects ECG signals of a heart and the event-determining unit, on the basis of the ECG signals detected by the detection unit and signals emitted by the stimulation control unit, determines whether a detected event represents a spontaneous or a stimulated event. The stimulation control unit ascertains a stimulation rate in dependence on a base rate and a physiological demand and alters the base rate in dependence on the event-determining unit in a first mode when atrial or ventricular events occur in such a way that in the case of a spontaneous atrial event a spontaneous interval is prolonged by a first change value, that in the case of a stimulated atrial event a base interval is prolonged by a second change value, and that in the case of a ventricular extrasystole a base interval is prolonged by a third change value, whereby in all cases the base rate is lowered. Alternatively or additionally the stimulation control unit is adapted to vary the base rate in a second mode when ventricular events occur in such a way that in the case of a spontaneous ventricular event the base rate is increased and in the case of a stimulated ventricular event the base rate is lowered. The lowering of the base rate in the second mode occurs abruptly in smaller steps than the increase in the base rate, which is also abrupt, in the case of detected natural (spontaneous) ventricular events. The stimulation unit stimulates the heart in accordance with the signals received from the stimulation control unit.

The advantages involved with the invention are in particular that translation of expert medical knowledge into a form which is viable for a cardiac pacemaker, that is to say minimal computing complication and expenditure for the cardiac pacemaker and thus the attainment of such translatability without substantially adversely affecting the (battery) life is achieved.

Accompanied by permanent and immediate therapy optimization (beat-to-beat algorithms) the cardiac pacemaker patient enjoys an enhancement in the quality of life, which under some circumstances is marked. The therapy improvements for the patient can be understood by virtue of extracorporal monitoring procedures (for example long-term surface ECG) (any heart activity and therewith also the algorithm functionality can be precisely analyzed).

In a preferred configuration of the invention the stimulation control unit is suitable for determining the base rate of the heart within predetermined limits. That ensures that the base rate of the heart does not fall below a critical value or rise above a critical value which can adversely affect the well-being or the health of the patient.

In a further embodiment of the invention the rate-adaptive cardiac pacemaker has an activity detection unit which is adapted to detect the activity of a patient and to deliver a corresponding activity signal. The stimulation control unit is connected to the activity detection unit and adapted to determine a base rate of a patient in accordance with a first or a second mode of operation in rate-adaptive manner in such a way that the base rate of the heart is reduced in accordance with the first mode of operation in a predetermined first step interval if the activity signal does not indicate any activity on the part of the patient within a predetermined first time interval and the base rate of the heart is increased in accordance with the second mode of operation in a predetermined second step interval if the activity signal indicates activity on the part of the patient within a predetermined second time interval. The first time interval in that respect is longer than the second time interval while the first step interval is identical to the second step interval.

Besides rate-adaptive control of the cardiac pacemaker in accordance with atrial or ventricular events the cardiac pacemaker thus also takes account of the activity on the part of the patient. When the patient is at rest the base frequency is lowered while it is raised again upon renewed activity.

The object of the invention is further attained by a rate-adaptive cardiac pacemaker as set forth in claim 4.

In this respect, the invention is based on the notion that the rate-adaptive cardiac pacemaker has an activity detection unit which is adapted to detect the activity of a patient and to output a corresponding activity signal and a stimulation control unit which is connected to the activity detection unit and which is adapted to determine a base rate of a patient in accordance with a first or a second mode of operation in rate adaptive manner in such a way that the base rate of the heart is lowered in accordance with the first mode of operation in a predetermined first step interval if the activity signal does not display activity on the part of the patient within a predetermined first time interval and the base rate of the heart is raised in accordance with the second mode of operation in a predetermined second step interval if the activity signal indicates activity on the part of the patient within a predetermined second time interval. The rate-adaptive cardiac pacemaker also has a stimulation unit which is connected to the stimulation control unit and is adapted to stimulate the heart in dependence on the output signal of the stimulation control unit, wherein the first time interval is longer than the second time interval and the first step interval is equal to the second step interval.

The advantages that this entails are in particular that the base frequency is lowered not abruptly but stepwise and is rapidly raised again upon detection of activity on the part of the patient so that the metabolic demand of the patient can be covered better and in a manner governed by situation and loading.

Further embodiments of the invention are the subject-matter of the appendant claims.

BRIEF DESCRIPTION OF THE DRAWINGS

Embodiments by way of example of the invention are described in greater detail hereinafter with reference to the drawing in which.

DETAILED DESCRIPTION OF A PREFERRED EMBODIMENT

Figure 1:
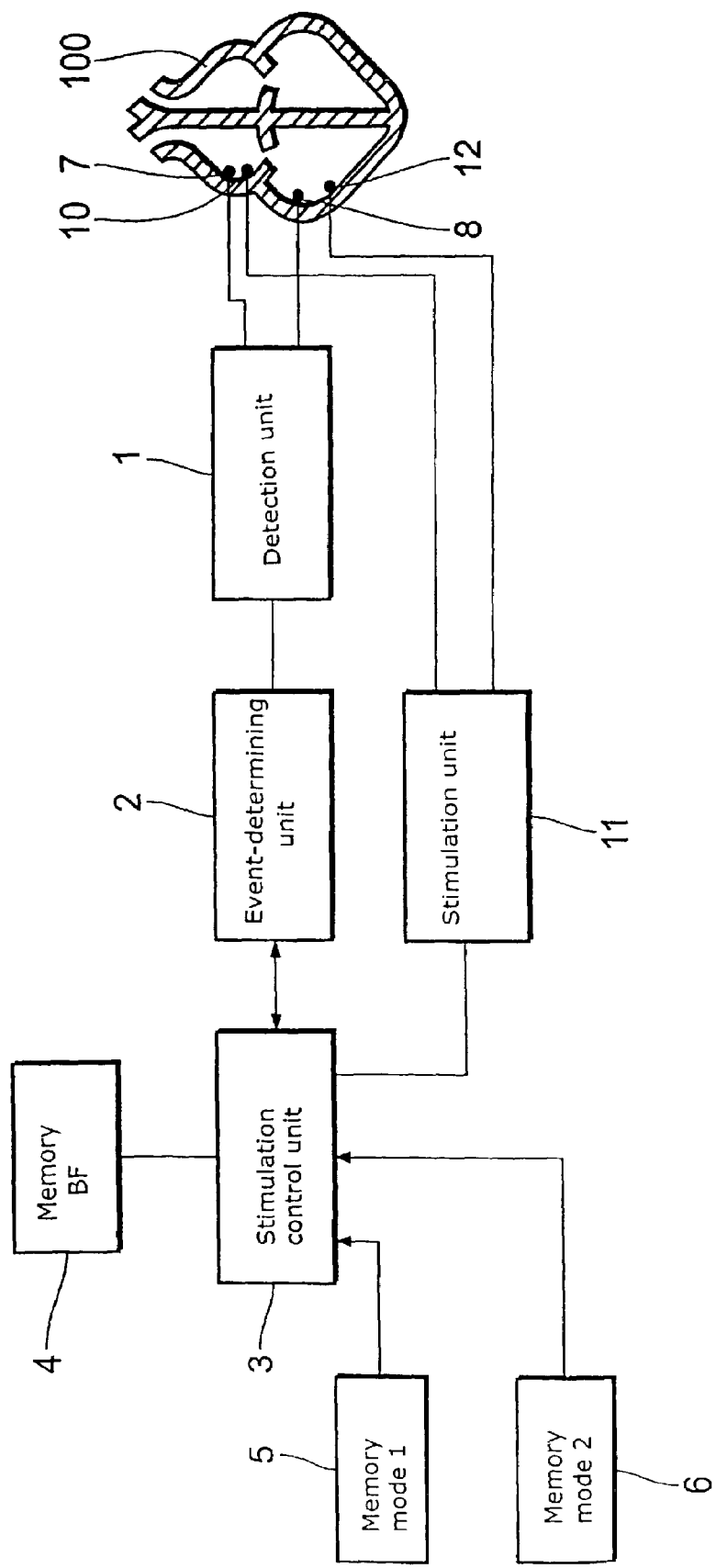
FIG. 1 shows a block circuit diagram of a rate-adaptive cardiac pacemaker in accordance with a first and a second embodiment.

FIG. 1 shows a rate-adaptive cardiac pacemaker in accordance with a first and a second embodiment. In this case the cardiac pacemaker has a detection unit 1, an event-determining unit 2, a stimulation control unit 3, a base frequency parameter memory 4, a memory 5 for the mode 1, a memory 6 for the mode 2 and a stimulation unit 11.

The detection unit 1 is connected on the one hand to two electrodes, of which one electrode 7 is in the atrium and one electrode 8 is in the ventricle, and on the other hand to the event-determining unit 2. The stimulation control unit 3 is connected to the event-determining unit 2, the base frequency parameter memory 4, the memory 5, the memory 6 and the stimulation unit 11. The stimulation unit 11 is connected to electrodes 10 and 12 in the atrium and ventricle respectively. Various associations of respective one or more electrodes in the atrium and ventricle with the detection unit 1 and the stimulation unit 11 are possible, optionally using change-over switches, so that per se known uni- or bipolar sensing and/or uni- or bipolar stimulation are possible.

The detection unit 1 detects the ECG signals of the heart 100 by means of the electrodes 7 and 8 and passes those signals to the event-determining unit 2. The event-determining unit 2 receives the ECG signals of the heart, which are outputted by the detection unit 1, and signals which are outputted by the stimulation control unit 3 and which indicate whether stimulation has taken place. On the basis of those received signals the event-determining unit 2 determines whether a detected event is a spontaneous event or a stimulated event. The result of that determining procedure is passed to the stimulation control unit 3. On the basis of that result the stimulation control unit 3 selects the mode 1 stored in the memory 5 or the mode 2 stored in the memory 6.

The memory 4 stores the patient-specific upper and lower limits of the base frequency $BF_{UL}$ and $BF_{LL}$ and if necessary the variable lower base frequency $BF_{LLvar}$ for the cardiac pacemaker.

The base frequency BF is to be kept as closely as possible below the natural frequency of the patient by means of the first embodiment of the rate-adaptive cardiac pacemaker shown in FIG. 1. The first embodiment corresponds in this respect to mode 1. As a result the cardiac pacemaker CPM does not intervene as standard, but compensatory pauses are interrupted after ventricular extrasystoles (VES) by a CPM stimulus. Essentially in that respect $Ap/(Ap+As) \approx VES$ component.

Suitable patients are preferably patients with a cardiac pacemaker in the DDD or AAI mode and with frequent ventricular and supraventricular extrasystoles (for example with the sick sinus syndrome, AV-blockages or HOCM). That can occur for example in the case of patients for example with an AV-block II°, type 2:1, dominant, with frequent VES.

A pacemaker in accordance with the first embodiment is not suitable however for patients with a base frequency which is set at a higher level, for example after AV-node ablation, patients with a high-level cardiac insufficiency without leg block, patients in regard to whom a high stimulation component is wanted (for example in the case of torsades) and patients with a cardiac pacemaker with a VDD- and VVI-mode, as this involves asynchronous ventricle stimulation when an atrium rhythm is maintained.

Re-adjustment of the base frequency to the current intrinsic cardiac frequency is intended to reduce the compensatory pauses without disturbing the intrinsic cardiac frequency pattern to a relatively great degree. That is of particular interest in relation to patients, in the case of whom a low base frequency was programmed and accordingly long compensatory pauses can occur without the pacemaker being able to intervene.

The base frequency is re-adjusted in such a way that it is as close as possible below the intrinsic cardiac frequency. Overall—except in the compensatory pauses after extrasystoles—stimulation should be effected as little as possible. At the same time care is taken to ensure that the base frequency BF is always within the defined limits base frequency LL, that is to say the lower base frequency, and base frequency UL, that is to say the upper base frequency.

The following input values must be predetermined by a doctor:

$BF_{LL}$ minimum permitted value for the base frequency (lower limit)

$BF_{UL}$ maximum permitted value for the base frequency (upper limit)

delta_ap change value after an Ap-event (an atrial pacing or stimulation event)

delta_as change value after an As-event (an atrial spontaneous event)

delta_ves change value after a VES-event.

Auxiliary values (internal variables):

$BI_{LL}$ minimum permitted value for the base interval (lower limit)

$BI_{UL}$ maximum permitted value for the base interval (upper limit)

BI base interval

ASI last atrial spontaneous interval (intrinsic and/or stimulated)

V_VES_I interval between last ventricular event (intr. or stimulated) and detected VES AV-delay cardiac pacemaker parameter The following values are set for initialization:

$BI_{LL}=60000/BF_{UL}$
$BI_{UL}=60000/BF_{LL}$

After each atrium action the following evaluation is started:

If As ⇒BI=ASI+delta_as (spontaneous atrial event)

If Ap ⇒BI=BI+delta_ap (stimulated atrial event)

If VES ⇒=BI=AV−delay+V_VES_I+delta_ves

If (BI<$BI_{LL}$) BI=$BI_{LL}$

If (BI>$BI_{UL}$) BI=$BI_{UL}$

If an atrial stimulation event is detected by the detection unit 1 and determined by the event-determining unit 2 the base interval BI is prolonged by the change value delta_ap after the $A_P$-event. If in contrast an atrial spontaneous event is detected by the detection unit 1 and determined by the event-determining unit 2 the spontaneous interval is prolonged by the change value delta_as after the $A_S$-event.

Subsequently a check is then made to ascertain whether the base interval BI is above the maximum permitted value for the base interval $BI_{UL}$ or below the minimum permitted value for the base interval $BI_{LL}$. If that is the case the base interval BI is raised or lowered respectively to the minimum permitted value or the maximum permitted value respectively for the base interval. That algorithm is executed after each atrium action, that is to say after a stimulation event or after a spontaneous event.

Figure 2:
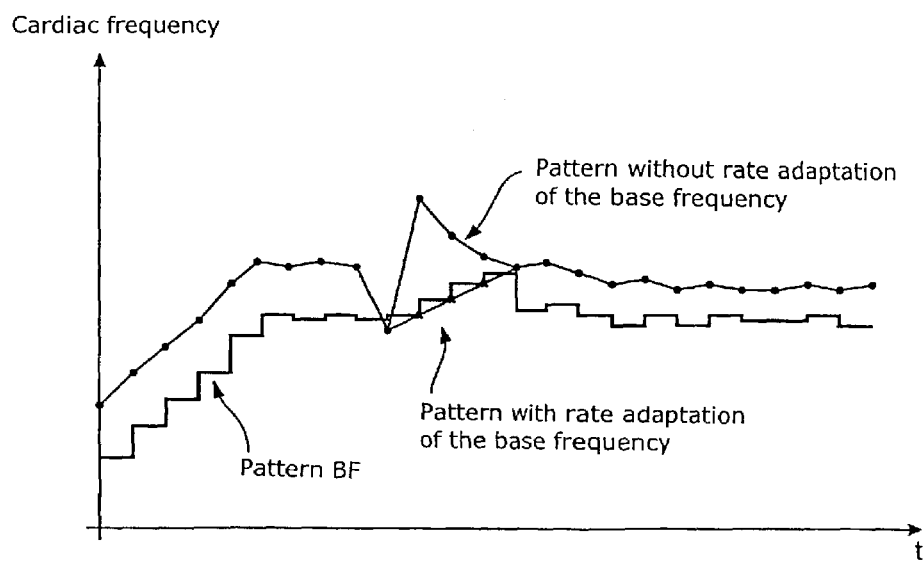
FIG. 2 shows a graph of the cardiac frequency of a patient with a rate-adaptive cardiac pacemaker in accordance with a first embodiment of FIG. 1, in relation to time.

FIG. 2 shows a graph in respect of cardiac frequency in relation to time. FIG. 2 shows both the configuration of the base frequency BF and also that of the cardiac frequency, more specifically both for the case without rate adaptation of the base frequency and also for the case of rate-adaptive re-adjustment of the base frequency. The second embodiment corresponds in this respect to mode 2. The pattern of the graph clearly shows that, in the case of a VES, the compensatory phase is interrupted on the basis of the re-adjusted base frequency BF by a stimulus.

The second embodiment of the rate-adaptive cardiac pacemaker shown in FIG. 1 is intended to suppress the conduction of fast atrial beats due to retrograde blockings of the AV-node, by permanent stimulation in the ventricle. At the same time however the base frequency BF should not be at an unnecessarily high value but it should be capable of being reduced to adapt it to the situation involved.

That can preferably be used in relation to patients with for example chronic atrial fibrillation and VVI-mode.

A cardiac pacemaker in accordance with the second embodiment in contrast is not suitable for patients with a maintained atrial rhythm or only intermittent atrial fibrillation, in relation to patients with a base frequency which is set high, for example after AV-node ablation, in the case of a CPM in the VDD- and DDD-mode as here with the atrial rhythm maintained that involves increased asynchronous ventricle stimulation and a CPM in the AAI-mode as there are no data about ventricle events.

It has been shown that in the case of patients with chronic atrial fibrillation a stimulation mode in which over 90% of the ventricular actions are stimulated results in stabilization of the cardiac frequency with the suppression of fast conducted beats.

The base frequency BF is re-adjusted in such a way that it is as close as possible above the intrinsic cardiac frequency. Essentially in that respect Vp/(Vp+Vs)≈100%. At the same time the stimulation control unit 3 controls the stimulation unit 11 in accordance with the data stored in the memory 4 in such a way that the base frequency is always within the defined limits, that is to say the base frequency $BF_{LL}$ as the minimum permitted value for the base frequency and base frequency $BF_{UL}$ as the maximum permitted value for the base frequency.

The following input values must be patient-specifically predetermined by a doctor:

$BF_{LL}$ minimum permitted value for the base frequency (lower limit)

$BF_{UL}$ maximum permitted value for the base frequency (upper limit)

delta_vp change value after a Vp-event (for example 1 ppm)

delta_vs change value after a Vs-event n_limit upper limit for internal counter (for example 10)

n_reinit re-initialization of the internal counter (for example 7).

Parameters:

BF base frequency

Auxiliary values (internal variables):

n counter

For initialization:

n is set=0.

After each ventricle action the following evaluation is started:

If Vp ⇒>n++ (stimulated ventricular event)
  if (n=n_limit) {BF=BF-delta_vp;n=n_reinit;}
  if (BF<$BF_{LL}$) {BF=$BF_{LL}$;}
If Vs ⇒n=0 (spontaneous ventricular event)
  BF=BF+delta_vs
  if (BF>$BF_{UL}$) f BF=$BF_{UL}$;)

The algorithm in accordance with the second embodiment of the invention is executed for each ventricle action and corresponds to the mode 2:

If a ventricular stimulated event Vs is detected by the detection unit 1 and determined by the event-determining unit 2 the counter n—which upon initialization was set to 0—is increased by 1. When the counter n has reached the value n_limit, for example 10, the base frequency BF is lowered by delta_vp, for example 1 ppm (pulse per minute) and the counter n is reset to n_reinit, for example 7. A check is then made to ascertain whether the base frequency BF is below the minimum permitted value for the base frequency $BF_{LL}$. If that is the case the base frequency BF is set to the minimum permitted value for the base frequency $BF_{LL}$.

If a spontaneous ventricular event $V_S$ is detected by the detection unit 1 and determined by the event-determining unit 2 the counter n is set to 0 and the base frequency BF is increased by delta_vs, for example 4 ppm. A check is then made to ascertain whether the base frequency BF is above the maximum permitted value for the base frequency $BF_{UL}$. If that is the case the base frequency BF is set to the maximum permitted value for the base frequency $BF_{UL}$.

Figure 3:
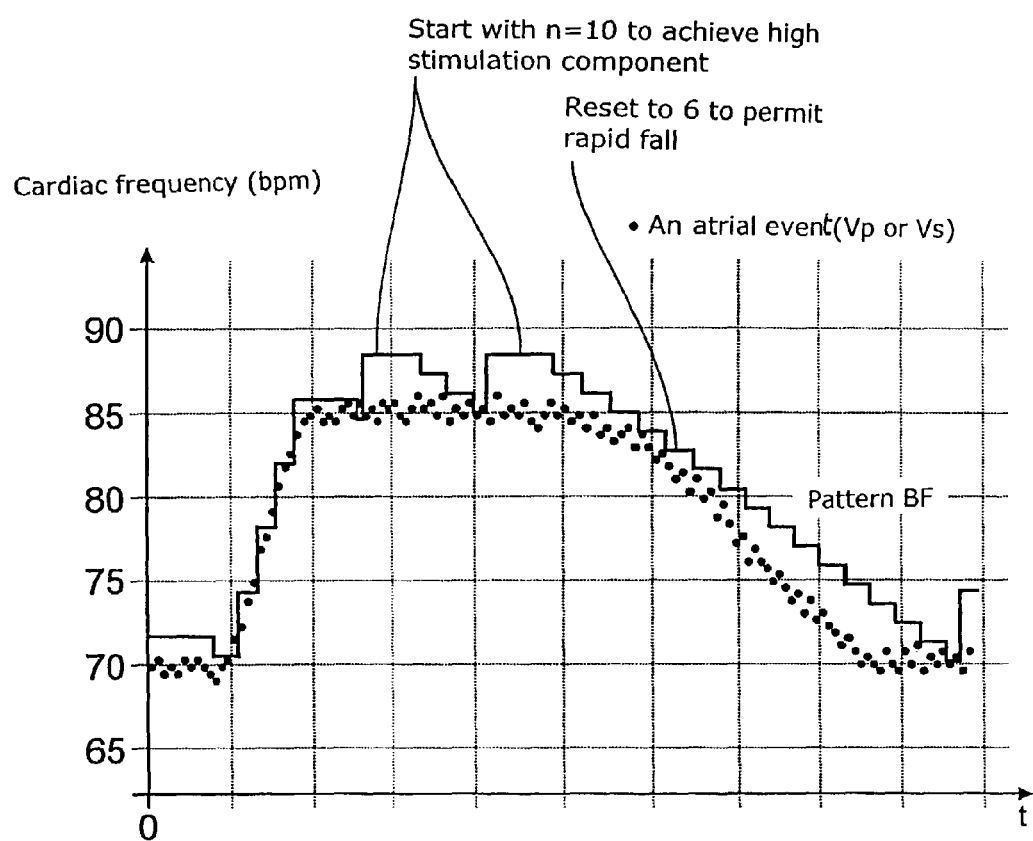
FIG. 3 shows a graph of the cardiac frequency of a patient with a rate-adaptive cardiac pacemaker in accordance with a second embodiment of FIG. 1, in relation to time.

FIG. 3 shows a graph in respect of cardiac frequency in relation to time. FIG. 3 represents both the pattern of the base frequency BF and also the ventricular events, wherein the ventricular events are illustrated as dots and the pattern of the base frequency BF is represented as a continuous line. The pattern of the graph clearly shows how the base frequency BF is adapted to the pattern of the ventricular events. In order to achieve a high stimulation component, a drop in the stimulation component is only initialized when the counter n has reached the value 10. Subsequent resetting of the counter n to 6 permits a rapid drop in the stimulation component.

Figure 4:
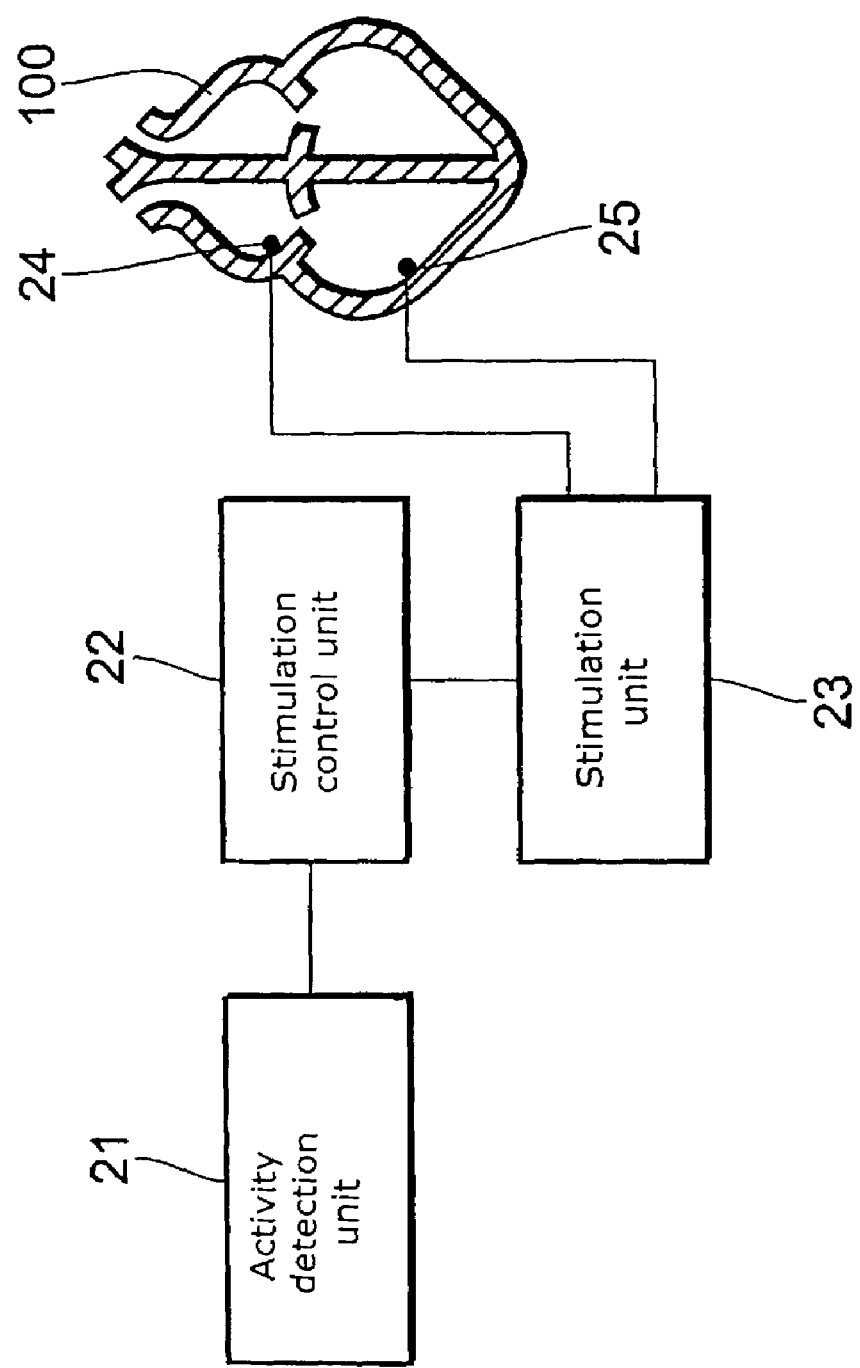
FIG. 4 shows a block circuit diagram of a rate-adaptive cardiac pacemaker in accordance with a third embodiment.

FIG. 4 shows a cardiac pacemaker in accordance with a third embodiment of the invention. In this case the cardiac pacemaker has a stimulation control unit 22, a stimulation unit 23 and an activity detection unit 21, wherein the stimulation control unit 22 is connected to the stimulation unit 23 and the activity detection unit 21. The stimulation unit 23 is in turn connected to the atrial electrode 24 and/or the ventricular electrode 25 and stimulates the heart in accordance with the control signals obtained from the stimulation control unit 22, by way of those electrodes.

The activity detection unit 21 can be for example an acceleration measuring unit or alternatively thereto also a respiration rate detection unit, as described in DE 197 47 820 or EP 0 449 401.

The disadvantages of a time-controlled (night) reduction in the base frequency BF when the patient is resting are to be replaced by an activity-controlled reduction. If the patient is at rest over a prolonged period of time the base frequency is lowered stepwise by a total of 10 ppm. As soon as activity is detected the base frequency is quickly raised again.

The rate-adaptive cardiac pacemaker in accordance with the third embodiment of the invention is suitable in particular for patients with sick sinus syndrome or for patients with chronic atrial fibrillation. The cardiac pacemaker however is not suitable for patients who require a high base frequency (for example after AV-node ablation or torsades), for patients with frequent SVES and VES (risk of prolonging the comp. pause) or for patients with the carotis sinus syndrome (insufficient rise in frequency during an episode).

The (night) reduction in the base frequency when the patient is at rest is not linked to rigid times but to the activity of the patient. In addition the base frequency is lowered not abruptly but stepwise.

If no activity is measured over a long period of time the base frequency is lowered stepwise. If activity is measured within a short period of time the base frequency is again raised stepwise to its old value.

The following input values must be predetermined by a doctor:

$BF_{LL}$ minimum permitted value for the base frequency (lower limit)
$BF_{UL}$ maximum permitted value for the base frequency (upper limit)
timer repetition value of the algorithm (time duration in seconds)
step change value (1, 2 or 5).

That therefore gives for example for the timer=60 s:

TABLE 1

| Step | Time duration for reduction by a total of 10 ppm | Time duration for increase by a total of 10 ppm |
| --- | --- | --- |
| 1 | 20 min (10 min + 10 min) | 11 min (1 min + 10 min) |
| 2 | 15 min (10 min + 5 min) | 6 min (1 min + 5 min) |
| 5 | 12 min (10 min + 2 min) | 3 min (1 min + 2 min) |

Parameter:
BF base frequency
Auxiliary values (internal variables):
$BF_{level}$ "level" of the base frequency (current state)
act(t) actual current degree of activity (value of the activity detection unit 21) at the time t
$mean\_act^n(t)$ mean value of the degree of activity of the last n minutes at the time t
min_act minimum degree of activity (min. value of the activity detection unit 21)
max_act maximum degree of activity (max. value of the activity detection unit 21)
$sum\_act^n$ sum of the activity values of the last n minutes
Initializations:
$BF_{level}$=10

In accordance with the value of the timer the following evaluation is effected by the stimulation control unit 22:

| | | |
| --- | --- | --- |
| Step 31: | $sum\_act^{10} = sum\_act^{10} + mean\_act^1(0) - mean\_act^1(-10\ min)$ | |
| Step 32: | $sum\_act^3 = sum\_act^3 + mean\_act^1(0) - mean\ act^1(-3\ min)$ | |
| Step 33: | if ($sum\_act^{10} \leq 11 *min\_act$) and ($BF_{level} >0$) | if (as good as) no activity in the last 10 min. and BF not yet completely reduced |
| | { | |

-continued

| Step 35: | if(BF ≧ BF$_{LL}$ + step) | if BF is still above the lower limit value |
|---|---|---|
| | { | |
| Step 36: | BF = BF − step | BF further lowered (in total by 10 ppm) |
| Step 37: | BF$_{level}$ =BF$_{level\ -\ step}$ | secure lowering level |
| | } | |
| Step 38: | to step 43 | |
| | } | |
| Step 34: | if(sum_act$^3$ > 4*min_act) and (BF$_{level}$ < 10) | if in the last 3 min. a (slight) activity and BF not yet completely raised |
| | { | |
| Step 39: | if (BF ≦ BF$_{UL}$ − step) | |
| | { | |
| Step 40: | BF = BF + step | further raise BF (in total by 10 ppm) |
| Step 41: | BF$_{level}$ = BF$_{level}$ + step | secure lowering level |
| | } | |
| Step 42: | to step 43 | |
| | } | |
| Step 43: | end of procedure (renewed call-up of step 31 after timer sec.). | |

Figure 5:
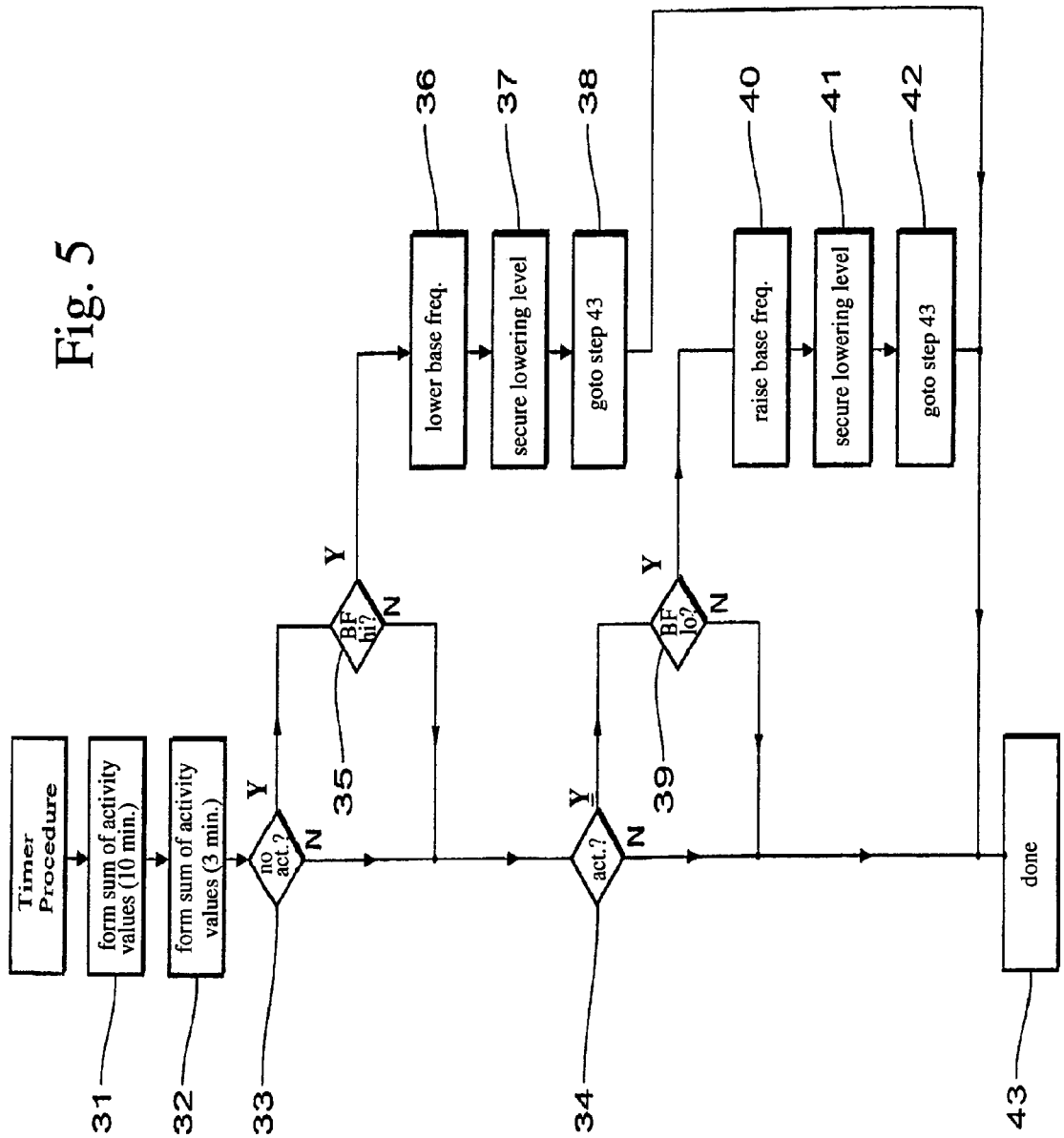
FIG. 5 shows a flow chart relating to control of the rate-adaptive cardiac pacemaker in accordance with the third embodiment in FIG. 4.

FIG. 5 shows a flow chart of an algorithm in accordance with the third embodiment of the invention. In step 31 the sum of the activity values of the last 10 minutes is formed, that is to say sum_act$^{10}$=sum_act$^{10}$+mean_act$^1$(0)−mean_act$^1$(−10 min), and in step 32 the sum of the activity values of the last three minutes is formed, that is to say sum_act$^3$=sum_act$^3$+mean_act$^1$(0)−mean_act$^1$(−3 min). If in step 33 (as good as) no activity is detected in the last 10 minutes and the base frequency BF$_{level}$ has not yet been completely lowered the flow proceeds to step 35. Otherwise the flow continues to step 34.

Step 35 involves checking whether the base frequency BF is still above the lower limit value. If that is not the case the flow goes on to step 34. Otherwise the flow proceeds to step 36. In step 36 the base frequency BF is further lowered by the change value step (in total by 10 ppm) and the flow proceeds to step 37. In step 37 the lowering level is secured and the flow proceeds to step 38. In step 38 the flow jumps to step 43.

Step 34 involves checking whether a (slight) activity is detected in the last 3 minutes and the base frequency has not yet been completely raised. If that is the case the flow proceeds to step 39, otherwise it goes to step 43.

Step 39 involves checking whether the base frequency BF is still below the upper limit value BF$_{UL}$. If that is the case the flow proceeds to step 40, otherwise it goes to step 43. In step 40 the base frequency BF is further raised by the change value step (in total by 10 ppm) and the flow proceeds to step 41 where the lowering level is secured. The flow then goes to step 42 in which the flow is passed to step 43.

The procedure terminates in step 43. After expiry of the set time (timer) the procedure is started afresh at step 31.

That algorithm is repeated in accordance with the value of the variable timer, for example every 60 seconds.

Figure 6:
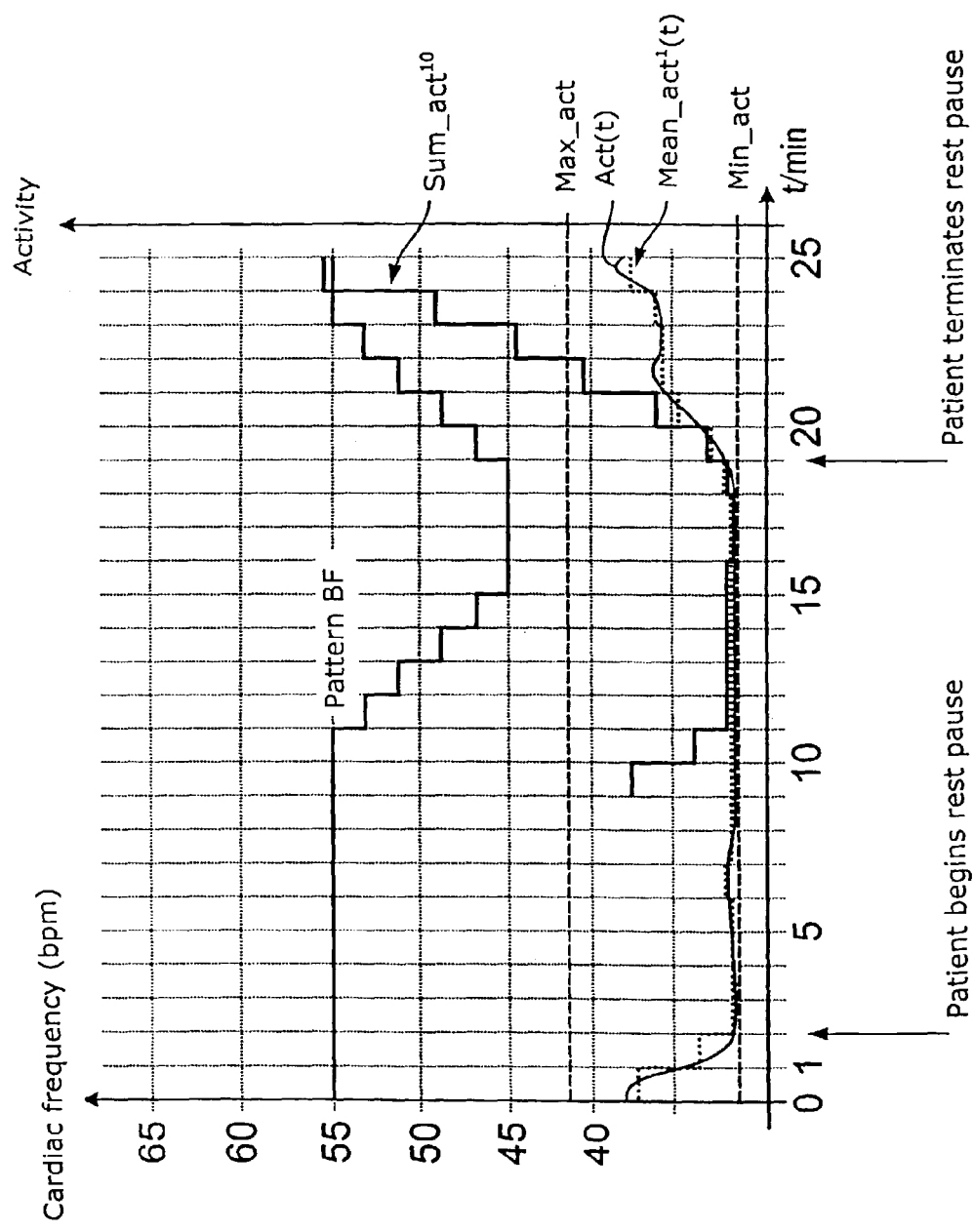
FIG. 6 shows a graph of the cardiac frequency of a patient with a rate-adaptive cardiac pacemaker in accordance with the third embodiment of FIG. 4, in relation to time.

FIG. 6 shows a graph in respect of the cardiac frequency of a patient with a rate-adaptive cardiac pacemaker in accordance with the third embodiment of FIG. 4. A fall in the base frequency during a rest pause on the part of the patient and the rise in the base frequency at the end of the rest pause can be clearly seen in this graph.

Figure 7:
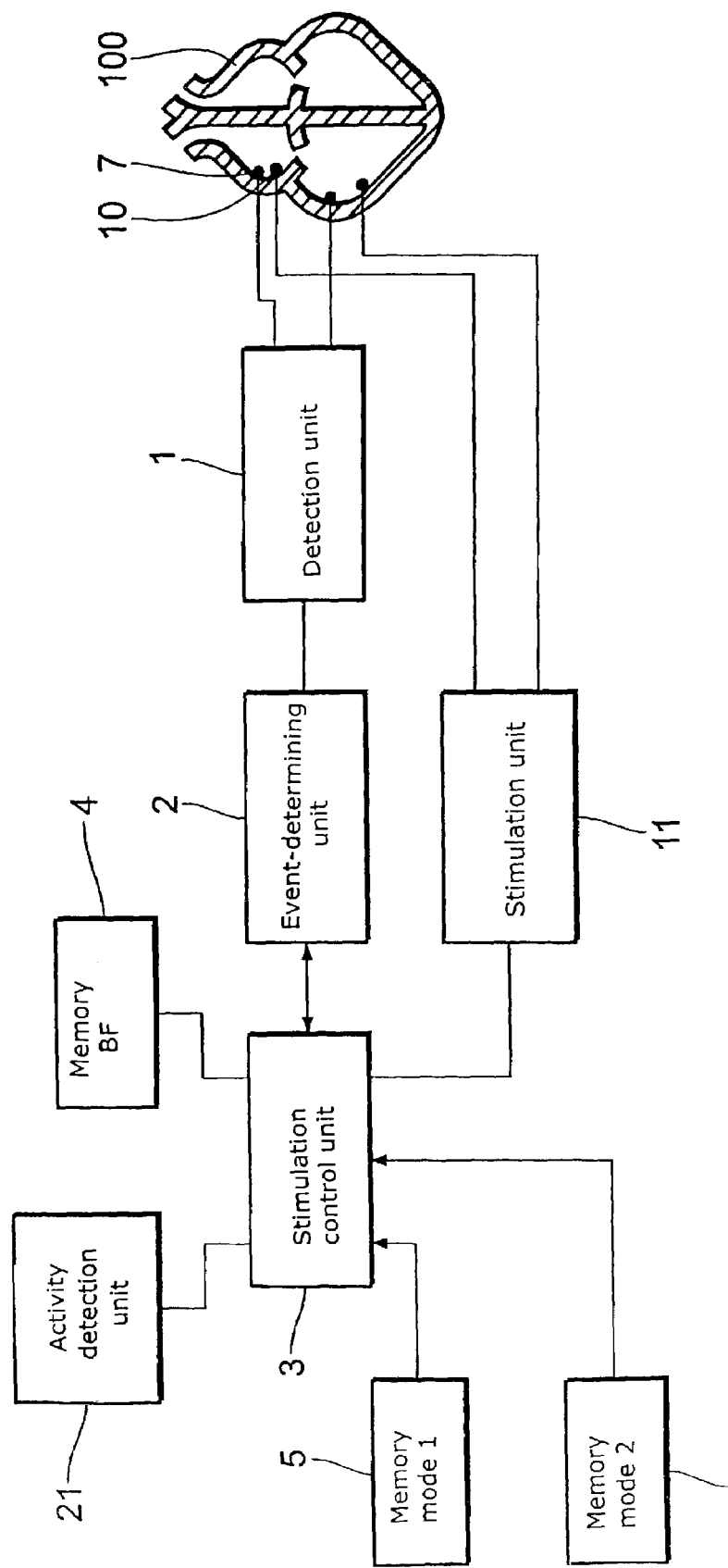
FIG. 7 shows a block circuit diagram of a rate-adaptive cardiac pacemaker in accordance with a fourth embodiment.

FIG. 7 shows a rate-adaptive cardiac pacemaker in accordance with a fourth embodiment of the invention. The structure of the cardiac pacemaker substantially corresponds to that of the cardiac pacemaker in accordance with the first embodiment of the invention shown in FIG. 1. In addition to the cardiac pacemaker shown in FIG. 1 the cardiac pacemaker in accordance with the fourth embodiment of the invention has an activity detection unit 21 which is connected to the stimulation control unit 3.

The detection unit 1 detects the ECG signals of the heart 100 by means of the electrodes 7 and 8 and passes those signals to the event-determining unit 2. The event-determining unit 2 receives the ECG signals of the heart which are outputted by the detection unit 1, and signals which are outputted by the stimulation control unit 3 and which indicate whether stimulation has occurred. On the basis of those received signals the event-determining unit 2 determines whether a detected event is a spontaneous event or a stimulated event. The result of that determining operation is passed to the stimulation control unit 3. On the basis of that result the stimulation control unit 3 selects the mode 1 stored in the memory 5 or the mode 2 stored in the memory 6.

The rate-adaptive cardiac pacemaker in accordance with the fourth embodiment substantially corresponds to a combination of the features of the cardiac pacemaker in accordance with the first embodiment and a cardiac pacemaker in accordance with the third embodiment of the invention. The essential difference is that the level of the base frequency is varied in dependence on the activity of the patient.

The base frequency BF is held as closely as possible below the intrinsic frequency of the patient. As a result the CPM does not intervene as standard, but compensatory pauses are interrupted after VES by a CPM stimulus. At the same time in rest pauses the minimum base frequency BF (lower limit value) is lowered stepwise by a total of 10 ppm. As soon as an activity is recognized the minimum base frequency is quickly raised again.

Suitable patients are preferably patients with a cardiac pacemaker in the DDD or MI-mode and with frequent ventricular and supraventricular extrasystoles (for example in the case of the sick sinus syndrome, AV-blockages or HOCM).

That can be used for example in relation to patients with an AV-block II°, type 2:1, dominant, with frequent VES.

Unsuitable patients are patients with a base frequency which set relatively high, for example after AV-node ablation, patients with high-level cardiac insufficiency without leg block, patients in relation to whom a high stimulation component is wanted, for example in the case of torsades, patients with a CPM in the VDD- and VVI-mode as here asynchronous ventricle stimulation occurs with the atrium rhythm being maintained, and patients with the carotis sinus syndrome (insufficient rise in frequency during an episode).

Re-adjustment of the base frequency to the current intrinsic cardiac frequency is intended to reduce the compensatory pauses without interfering with the intrinsic cardiac frequency pattern to a major degree. That is of interest in particular in relation to patients, in relation to whom a low base frequency was programmed and accordingly long compensatory pauses can occur without the pacemaker being able to intervene.

At the same time the (night) reduction in the base frequency when the patient is at rest is not linked to rigid times but to the activity of the patient. In addition the base frequency is lowered not abruptly but stepwise.

The base frequency is so re-adjusted that it is as close as possible below the intrinsic cardiac frequency. Overall— except in the compensatory pauses after extrasystoles— stimulation should be effected as little as possible.

At the same time care is taken to provide that the base frequency is always within the defined limits, a base frequency UL as the minimum permitted value for the base frequency $BF_{UL}$ and the base frequency LL+10 ppm (with activity) or base frequency LL (at rest).

If no activity is measured over a long period of time the lower limit is reduced stepwise by a total of 10 ppm so that the base frequency can also be further lowered. If activity is measured within a short period of time the lower limit is raised again stepwise to its old value, whereby the re-adjusted base frequency can no longer assume those low values.

The following input values must be patient-specifically predetermined by a doctor:

$BF_{UL}$ minimum permitted value for the base frequency (upper limit)

$BF_{LL}$ minimum permitted value for the base frequency (lower limit)

delta_ap change value after an Ap-event delta_as change value after an As-event delta_ves change value after a VES-event timer repetition of the algorithm (time duration in seconds)

step change value (1, 2 or 5).

That thus gives for example for timer=60 s:

TABLE 2

| Step | Time duration for reduction by a total of 10 ppm | Time duration for increase by a total of 10 ppm |
| --- | --- | --- |
| 1 | 20 min (10 min + 10 min) | 11 min (1 min + 10 min) |
| 2 | 15 min (10 min + 5 min) | 6 min (1 min + 5 min) |
| 5 | 12 min (10 min + 2 min) | 3 min (1 min + 2 min) |

Parameter:

BF base frequency

Auxiliary values (internal variables):

BI base interval $BI_{LL}$ minimum permitted value for the base interval (lower limit)

$BI_{UL}$ maximum permitted value for the base interval (upper limit)

ASI last atrial spontaneous interval (intrinsic and/or stimulated)

V_VES_I interval between last ventricular event (intr. or stim.) and detected VES AV-delay CPM parameter $BF_{LL.var}$ minimum permitted value for the base frequency (lower limit with activity)

$BF_{level}$ "level" of the base frequency (current state)

act(t) actual current degree of activity (value of the activity detection unit 21) at the time t mean_act$^n$(t) mean value of the degree of activity of the last n minutes at the time t min_act minimum degree of activity (min. value of the activity detection unit 21)

max_act maximum degree of activity (max. value of the activity detection unit 21)

sum_act$^n$ sum of the activity values of the last n minutes

Initializations:

$BF_{level}$=10

$BF_{LL.var}$=$BF_{LL}$+10 ppm $BI_{UL}$=60000/$BF_{LL.var}$ $BI_{LL}$=60000/$BF_{UL}$ The following evaluation is started after each atrium action:

If Ap ⇒ BI=B+delta_ap

If As ⇒ BI=ASI+delta_as

If VES ⇒ =BI=AV-delay+V_VES_I+delta_ves

If (BI<$BI_{LL}$) BI=$BI_{LL}$

If (BI>$BI_{UL}$) BI=$BI_{UL}$

The following evaluation is effected in accordance with the value of timer:

| | | |
| --- | --- | --- |
| Step 51: | sum_act$^{10}$ = sum_act$^{10}$ + mean_act$^1$ (0) − mean_act$^1$(−10 min) | |
| Step 52: | sum_act$^3$ = sum_act$^3$ + mean_act$^1$ (0) − mean act$^1$(−3 min) | |
| Step 53: | if (sum_act$^{10}$ ≦ 11*min_act) and ($BF_{level}$ > 0) | If (as good as) no activity in the last 10 min. and BF not yet completely lowered |
| | { | |
| Step 55: | if ($BF_{LL.var}$ ≧ $BF_{LL}$ + step) | If BF is still above the lower limit value |
| | { | |
| Step 56: | $BF_{LL.var}$ = $BF_{LL.var}$ − step | BF further lowered (in total by 10 ppm) |
| Step 57: | $BF_{level}$ = $BF_{level}$ − step | Secure lowering level |
| | } | |
| | to step 61 | |
| | } | |

-continued

| Step 54: | if (sum_act³ > 4*min_act) and (BF$_{level}$ < 10) | If in the last 3 min. a (slight) activity and BF not yet completely raised |
|---|---|---|
| | { | |
| Step 58: | if(BF$_{LL.var}$ ≤ BF$_{UL.}$ – step) | If BF is still below the upper limit value |
| | { | |
| Step 59: | BF$_{LL.var}$ = BF$_{LL.var}$ + step | Further raise BF (in total by 10 ppm) |
| Step 60: | BF$_{level}$ = BF$_{level}$ + step | Secure lowering level |
| | } to step 61 } | |
| Step 61: | BI$_{UL}$ = 60000/BF$_{LL.var}$ | Implement changes for beat-to-beat algorithm |
| Step 62: | end of the processing (renewed call-up of step 51 after timer sec.). | |

Figure 8:
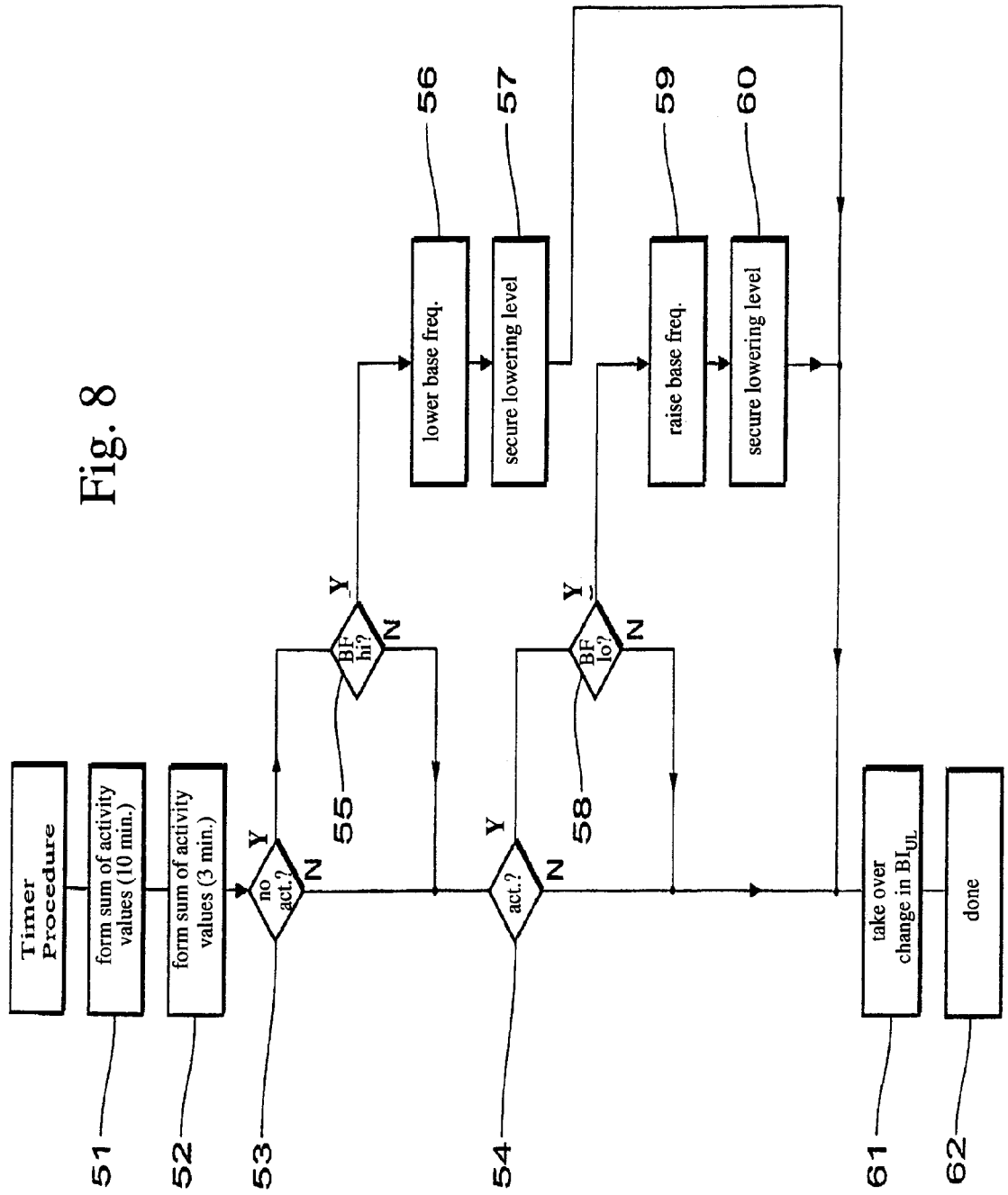
FIG. 8 shows a flow chart relating to control of the rate-adaptive cardiac pacemaker in accordance with the fourth embodiment in FIG. 6.

FIG. 8 shows a flow chart of an algorithm in accordance with the fourth embodiment of the invention. In step 51 the sum of the activity values of the last 10 minutes is formed, that is to say sum_act$^{10}$=sum_act$^{10}$+mean_act$^1$(0)–mean_act$^1$(–10 min), and in step 52 the sum of the activity values of the last three minutes is formed, that is to say sum_act$^3$=sum_act$^3$+mean_act$^1$(0)— mean_act$^1$(–3 min). If in step 53 (as good as) no activity is detected in the last 10 minutes and the base frequency BF$_{level}$ has not yet been completely lowered the flow proceeds to step 55. Otherwise the flow continues to step 54.

Step 55 involves checking whether the base frequency BF is still above the lower limit value. If that is not the case the flow goes on to step 54. Otherwise the flow proceeds to step 56. In step 56 the base frequency BF is further lowered by the change value step (in total by 10 ppm) and the flow proceeds to step 57. In step 57 the lowering level is secured and the flow proceeds to step 61.

Step 54 involves checking whether a (slight) activity is detected in the last 3 minutes and the base frequency has not yet been completely raised. If that is the case the flow proceeds to step 58, otherwise it goes to step 61.

Step 58 involves checking whether the base frequency BF is still below the upper limit value BF$_{UL}$. If that is the case the flow proceeds to step 59, otherwise it goes to step 61. In step 59 the base frequency BF is further raised by the change value step (in total by 10 ppm) and the flow proceeds to step 60 where the lowering level is secured. The flow then goes to step 61. Step 61 involves taking over the change in the upper limit of the base interval BI$_{UL}$ for the beat-to-beat algorithm.

The procedure terminates in step 62. After expiry of a set time (timer) the procedure is started afresh at step 51.

That algorithm is repeated in accordance with the value of the variable timer, for example every 60 seconds.

Figure 9:
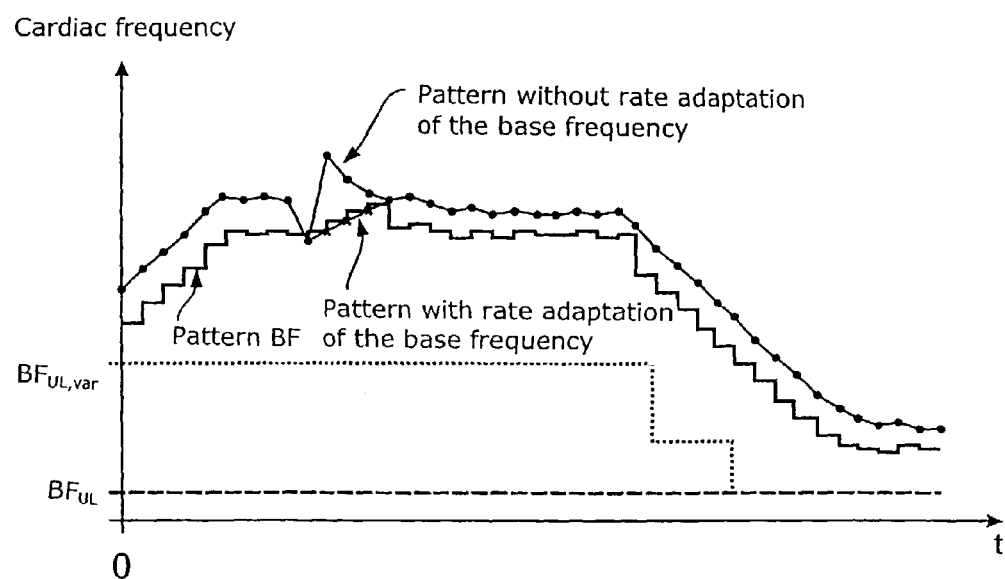
FIG. 9 shows a graph of the cardiac frequency of a patient with a rate-adaptive cardiac pacemaker in accordance with the fourth embodiment of FIG. 7, in relation to time.

FIG. 9 shows the frequency pattern of a heart in relation to time for a cardiac pacemaker in accordance with the fourth embodiment. The configuration of the cardiac frequency without rate adaptation of the base frequency is illustrated by dots and the configuration of the rate-adapted base frequency BF is represented as a continuous line. FIG. 9 also shows the upper and the lower base frequencies BF$_{LL}$, BF$_{UL}$, as well as the variable lower base frequency BF$_{LL.var}$.

It is worth-noting in this respect in particular how the variable lower base frequency BF$_{LL.var}$ is lowered with progressing time and continuing absence of activity.

The invention claimed is:

1. A rate-adaptive cardiac pacemaker comprising:
  a detection unit;
  an event-determining unit;
  a stimulation control unit; and
  a stimulation unit;
  wherein the event-determining unit is connected to the detection unit and the stimulation control unit, and the stimulation unit is connected to the stimulation control unit;
  wherein the detection unit is adapted to detect ECG signals of a heart;
  wherein the event-determining unit is adapted to determine whether a detected event represents a spontaneous or a stimulated event, on the basis of the ECG signals detected by the detection unit and the signals emitted by the stimulation control unit; and
  wherein the stimulation control unit is adapted to determine a stimulation rate depending upon a base rate and a physiological demand, and to vary the base rate at each detected natural or stimulated event based upon the determination of the event-determining unit;
  said stimulation control unit being in a first mode when atrial events occur in such a way that in the case of a spontaneous atrial event a spontaneous interval is prolonged by a first change value and that in the case of a stimulated atrial event a base interval is prolonged by a second change value, whereby in both cases the base rate is lowered, and
  said stimulation control unit being in a second mode when ventricular events occur to vary the base rate in such a way that in the case of a spontaneous ventricular event the base rate is raised by a third change value and in the case of a stimulated ventricular event the base rate is lowered by a fourth change value which is smaller than the third change value, and
  wherein the stimulation unit is adapted to stimulate the heart in accordance with the signals received from the stimulation control unit.

2. The rate-adaptive cardiac pacemaker as set forth in claim 1, wherein in the first mode, upon an occurrence of a ventricular extrasystole (VES), a base interval is prolonged by a fifth change value (delta_ves), whereby the base rate is lowered.

3. The rate-adaptive cardiac pacemaker as set forth in claim 1, wherein the stimulation control unit is adapted to determine the base rate of the heart within predetermined limits.

4. The rate-adaptive cardiac pacemaker as set forth in claim 1, wherein the stimulation control unit is adapted to control the stimulation unit based upon each atrial or ventricular event.

5. The rate-adaptive cardiac pacemaker as set forth in claim 2, wherein the stimulation control unit is adapted to determine the base rate of the heart within predetermined limits.

* * * * *